(12) United States Patent
Smith et al.

(10) Patent No.: US 10,376,316 B2
(45) Date of Patent: Aug. 13, 2019

(54) RETRACTABLE TISSUE CUTTING DEVICE

(71) Applicant: BOSTON SCIENTIFIC SCIMED, INC., Maple Grove, MN (US)

(72) Inventors: Paul Smith, Smithfield, RI (US); Robert Charles, New Boston, NH (US); Jon Taylor, Groton, MA (US); Daniel E. Hamilton, Mont Vernon, NH (US); Samuel Raybin, Marlborough, MA (US); Robert B. Devries, Northborough, MA (US); Niklas Andersson, Wayland, MA (US); Meghan Elizabeth Soens, Paris (FR); Mary Ann Cornell, Brimfield, MA (US); Ray H. Tong, Foxboro, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 378 days.

(21) Appl. No.: 15/294,067

(22) Filed: Oct. 14, 2016

(65) Prior Publication Data
US 2017/0119460 A1    May 4, 2017

Related U.S. Application Data

(60) Provisional application No. 62/247,387, filed on Oct. 28, 2015.

(51) Int. Cl.
*A61B 18/24* (2006.01)
*A61B 18/14* (2006.01)
(Continued)

(52) U.S. Cl.
CPC .......... *A61B 18/24* (2013.01); *A61B 18/1492* (2013.01); *A61B 2018/00601* (2013.01);
(Continued)

(58) Field of Classification Search
CPC ... A61B 17/29; A61B 17/00234; A61B 18/24; A61B 2018/00601; A61B 1/0676; A61B 2017/00296; A61B 2017/0034
See application file for complete search history.

(56) References Cited

U.S. PATENT DOCUMENTS 5,007,908 A * 4/1991 Rydell ............... A61B 18/1477
606/47
5,250,065 A * 10/1993 Clement ........ A61B 17/320016
600/571
(Continued)

FOREIGN PATENT DOCUMENTS

EP    1 849 416    10/2007
GB    2 311 468    10/1997
(Continued)

*Primary Examiner* — Linda C Dvorak
*Assistant Examiner* — Annabeth E Rodriguez
(74) *Attorney, Agent, or Firm* — Fay Kaplun & Marcin, LLP

(57) ABSTRACT

A tissue cutting device includes a flexible elongate body including a channel extending therethrough, a distal member connected to a distal end of the elongate body. The distal member includes a lumen extending therethrough in communication with the channel and a recess extending through an exterior surface of the distal member along a portion of a length thereof. The recess extends includes a receiving structure at a distal end thereof. A cutting element is slidably received within the channel and the lumen so that the cutting element is movable between an open tissue-receiving configuration and a closed tissue-gripping configuration, in which a distal portion of the cutting element extends across the recess such that the distal end of the cutting element is received within the receiving structure, a portion of a length of the distal portion extending radially beyond an exterior surface of the distal member.

20 Claims, 2 Drawing Sheets

(51) Int. Cl.
 *A61B 18/00* (2006.01)
 *A61B 18/18* (2006.01)
 *A61B 18/12* (2006.01)

(52) U.S. Cl.
 CPC . *A61B 2018/1266* (2013.01); *A61B 2018/144* (2013.01); *A61B 2018/1475* (2013.01); *A61B 2018/1807* (2013.01)

(56) References Cited

U.S. PATENT DOCUMENTS

| | | | |
|---|---|---|---|
| 6,540,695 B1 * | 4/2003 | Burbank | A61B 10/0266 |
| | | | 600/564 |
| 6,689,145 B2 | 2/2004 | Lee et al. | |
| 6,994,677 B1 | 2/2006 | Buehlmann et al. | |
| 8,162,966 B2 * | 4/2012 | Connor | A61B 17/320016 |
| | | | 606/160 |
| 8,287,535 B2 | 10/2012 | de la Mora Levy et al. | |
| 2008/0249553 A1 | 10/2008 | Gruber et al. | |
| 2015/0126994 A1 | 5/2015 | Matsui et al. | |

FOREIGN PATENT DOCUMENTS

| | | |
|---|---|---|
| JP | 2006-518656 | 8/2006 |
| WO | 2001/028446 | 4/2001 |
| WO | 2014/091846 | 1/2017 |

* cited by examiner

RETRACTABLE TISSUE CUTTING DEVICE

PRIORITY CLAIM

This application claims priority to U.S. Provisional Patent Application Ser. No. 62/247,387 filed Oct. 28, 2015; the disclosure of which is incorporated herewith by reference.

BACKGROUND

Physicians have been increasingly willing to perform more aggressive interventional and therapeutic endoscopic procedures including, for example, the removal of larger lesions (e.g., cancerous masses), tunneling under the mucosal layer of the gastrointestinal (GI) tract to treat tissue below the mucosa, full thickness removal of tissue, the treatment of issues of other organs by penetrating and passing out of the GI tract, and the endoscopic treatment/repair of post-surgical issues (e.g., post-surgical leaks, breakdown of surgical staple lines, anastomotic leaks). Using currently available tools, these complex procedures may be time consuming. For example, a conventional cautery knife generally requires precise control of an endoscope through which it is inserted as imprecise movements may result in unintended cuts.

SUMMARY

The present disclosure relates to a tissue cutting device, comprising a flexible elongate body extending longitudinally from a proximal end to a distal end and including a channel extending longitudinally therethrough, a distal member connected to the distal end of the elongate body, the distal member including a lumen extending therethrough in communication with the channel and a recess extending through an exterior surface of the distal member along a with the channel and a recess extending through an exterior surface of the distal member along a portion of a length thereof, the recess extending from a proximal end to a distal end which includes a receiving structure, and a cutting element slidably received within the channel and the lumen so that the cutting element is movable between an open tissue-receiving configuration, in which a distal end of the cutting element is proximal of the recess, and a closed tissue-gripping configuration, in which a distal portion of the cutting element extends across the recess such that the distal end of the cutting element is moved toward the distal end of the recess to be received within the receiving structure, a portion of a length of the distal portion extending radially beyond an exterior surface of the distal member.

In an embodiment, the cutting element may be connected to an energy source at a proximal end thereof so that energy is provided along a length thereof to cut tissue via the distal end of the cutting element.

In an embodiment, the energy source may be one of a radio frequency, a monopolar or bipolar AC or DC current, a laser, and an ultrasonic or infrasonic energy.

In an embodiment, the receiving structure may be one of a pocket and a groove.

In an embodiment, the receiving structure may be shaped to prevent the cutting element from being dislodged therefrom when a tissue received within the recess applies a force to the cutting element.

In an embodiment, the distal portion of the cutting element, in the closed configuration, may have a curved configuration in which the distal portion extends distally out of the lumen and curves outward beyond an exterior surface of the distal member, the distal end of the cutting element curving back toward the receiving structure of the recess.

In an embodiment, the exterior surface of the distal member may include a trough to support the cutting element in the curved configuration to maintain an orientation and a planar directional movement of the cutting element to the elongate body.

In an embodiment, the distal portion of the cutting element may be substantially hook-shaped.

In an embodiment, the receiving structure may be electrically insulated.

In an embodiment, the energy source may be a bipolar current. In such an embodiment, the receiving structure may be a return path for conducting electrical energy.

In an embodiment, the cutting element may be keyed to the lumen to maintain an orientation and a planar directional movement relative thereto.

The present disclosure also relates to a device for cauterizing tissue, comprising an elongate body extending longitudinally from a proximal end to a distal end and including a channel extending longitudinally therethrough, a distal member connected to the distal end of the elongate body, the distal member including a lumen extending therethrough in communication with the channel and a recess extending through an exterior surface of the distal member along a portion of a length thereof, the recess extending from a proximal end to a distal end which includes a receiving structure, a cutting wire slidably received within the channel and the lumen so that the cutting wire is movable between an open tissue-receiving configuration, in which a distal end of the cutting wire is proximal of the recess, and a closed tissue-gripping configuration, in which a distal portion of the cutting wire extends across the recess such that the distal end of the cutting wire is moved toward the distal end of the recess to be received within the receiving structure, and an energy source connected to the proximal end of the cutting wire to provide an electrical current therethrough so that the distal end of the cutting wire cuts a target tissue gripped between the distal end of the cutting wire and the distal end of the recess in the closed tissue-gripping configuration.

In an embodiment, the distal portion of the cutting element, in the closed configuration, may have a curved configuration in which the distal portion extends distally out of the lumen and curves outward beyond an exterior surface of the distal member, the distal end of the cutting element curving back toward the receiving structure of the recess.

In an embodiment, the cutting wire may be keyed to the lumen of the distal member to maintain an orientation and a planar directional movement of the cutting wire relative to the distal member.

In an embodiment, the receiving structure may be electrically insulated.

The present disclosure also relates to a method for cutting tissue, comprising inserting a cutting device into a living body to a target tissue via a working channel of an endoscope, the cutting device including a distal member having a lumen extending through a portion thereof and a recess extending through an exterior surface along a portion of a length thereof, receiving the target tissue in the recess of the distal member, moving a cutting element which is slidably received within the distal member from an open configuration, in which a distal end of the cutting element is proximal of the recess, to a closed configuration, in which a distal portion of the cutting element extends across the recess such that the distal end of the cutting element is moved toward the distal end of the recess to be received within a receiving structure at the distal end of the recess to grip the target tissue therebetween, and applying an energy along a length of the cutting element to cut the target tissue received within the recess.

In an embodiment, the method may further comprise moving the device one of laterally and or proximally relative to the endoscope to cut tissue.

In an embodiment, the method may further comprise rotating the device about a longitudinal axis thereof to excise an annular portion of tissue.

In an embodiment, a distal portion of the cutting element, in the closed configuration, may have a curved configuration in which the distal portion extends distally out of the lumen and curves outward beyond an exterior surface of the distal member, the distal end of the cutting element curving back toward the receiving structure of the recess.

In an embodiment, the cutting wire is keyed to the lumen of the distal member to maintain an orientation and a planar directional movement of the cutting wire relative to the distal member

DETAILED DESCRIPTION

Figure 1:
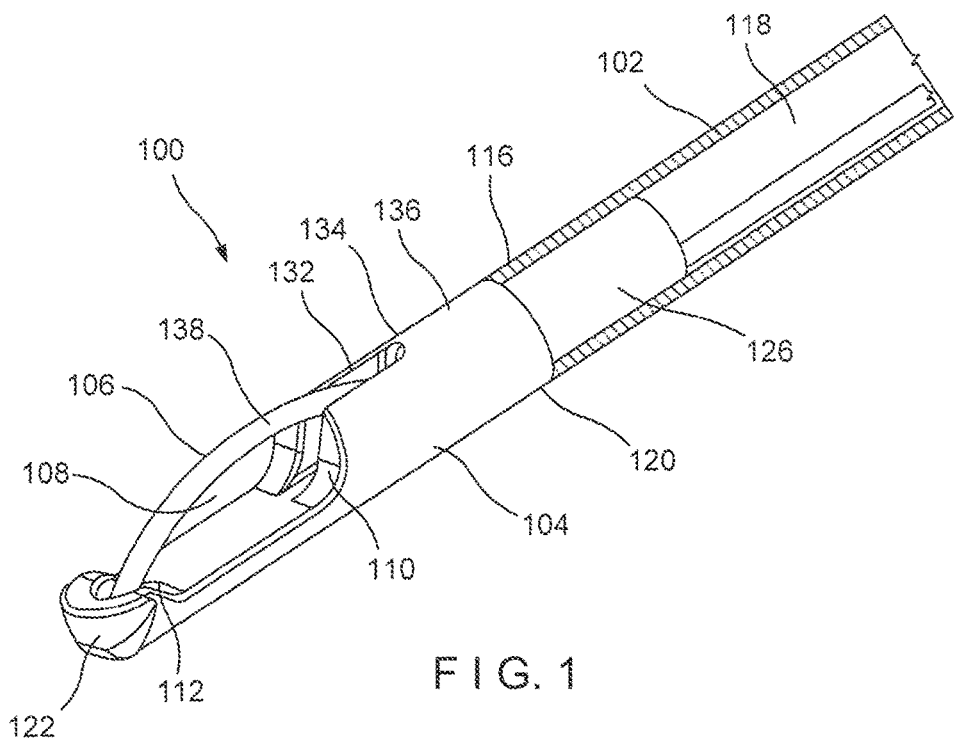
FIG. 1 shows a perspective view of a device according to an exemplary embodiment of the present disclosure.

The present disclosure may be further understood with reference to the following description and the appended drawings, wherein like elements are referred to with the same reference numerals. The present disclosure is directed to devices for the treatment of tissue and, in particular, endoscopic tissue cutting devices. Exemplary embodiments of the present disclosure describe a device for cutting tissue, the device including a retractable cutting element and a distal receiving feature for limiting the extension of a cutting edge of the cutting element to reduce the risk of unintended cuts. It should be noted that the terms "proximal" and "distal," as used herein, are intended to refer to a direction toward (proximal) and away from (distal) a user of the device.

Figure 2:
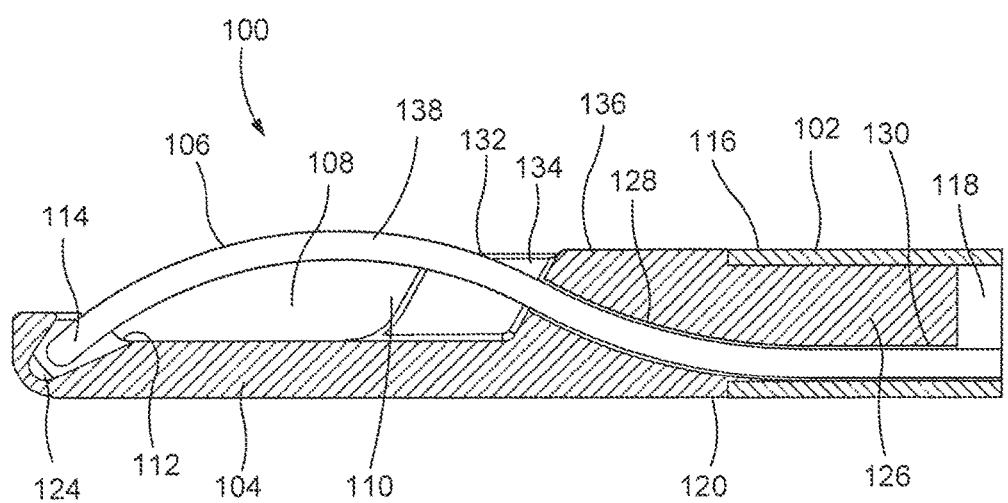
FIG. 2 shows a longitudinal cross-sectional view of the device of FIG. 1.
Figure 3:
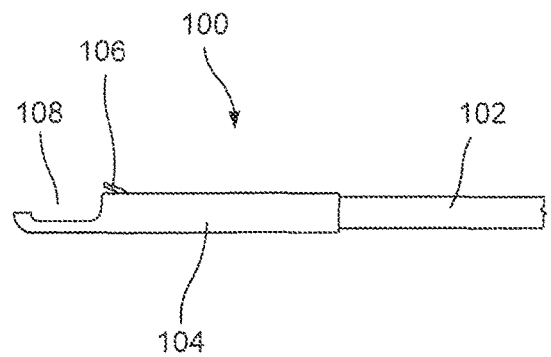
FIG. 3 shows a longitudinal side view of the device of FIG. 1, in an open configuration.
Figure 4:
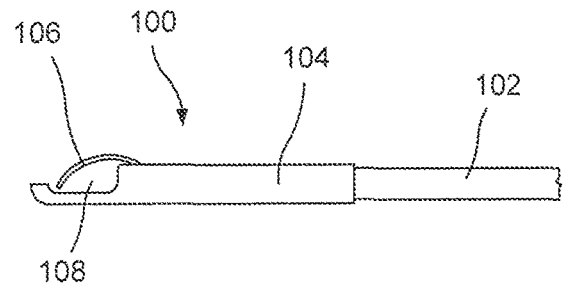
FIG. 4 shows a longitudinal side view of the device of FIG. 1, in a closed configuration.

As shown in FIGS. 1-5, a device 100 for cutting tissue comprises an elongate body 102 and a distal member 104 connected thereto. A cutting element 106 slidably extends through the elongate body 102 and the distal member 104 such that the cutting element 106 is movable between an open tissue receiving configuration and a closed tissue gripping configuration. The distal member 104 includes an elongate recess 108 extending along a length thereof from a proximal end 110 to a distal end 112. In the open configuration, as shown in FIG. 3, a distal end 114 of the cutting element 106 is proximate the proximal end 110 of the elongate recess 108 so that target tissue may be received within the recess 108 between the distal end 112 thereof and the distal end 114 of the cutting element 106. In the closed configuration, as shown in FIG. 4, the cutting element 106 is positioned distally with respect to the distal member 104 so that the distal end 114 of the cutting element 106 is adjacent the distal end 112 of the recess 108 gripping target tissue in the recess 108 between the cutting element 106 and the distal member 104. The gripped tissue may then be cut away from surrounding tissue by applying energy to the distal end 114 of the cutting element 106 as will be described in more detail below. Once the target tissue has been cut, the device 100 may be removed from the body so that a separate device may be inserted through the working channel to retrieve the cut tissue. The cut tissue may be retrieved using devices such as nets, bags or other retrieval devices. In another embodiment, the cutting element 106 may be used to grip or harpoon the cut tissue and drag the cut tissue out of the body. Energy options may include radio frequency, monopolar or bipolar AC or DC current, laser, ultrasonic or infrasonic energy.

The elongate body 102 extends longitudinally from a proximal end (not shown) to a distal end 116 and includes a channel 118 extending therethrough. The elongate body 102 according to this embodiment is sized and shaped to be passed through, for example, a working channel of an endoscope to reach a site within the body at which a target tissue is to be cut. The elongate body 102 according to this embodiment is sufficiently flexible to permit the elongate body 102 to be navigated through even tortuous paths of a living body (e.g., through a natural body lumen accessed via a natural bodily orifice). In one exemplary embodiment, the elongate body 102 may be, for example, an endoscopic catheter.

Figure 5:
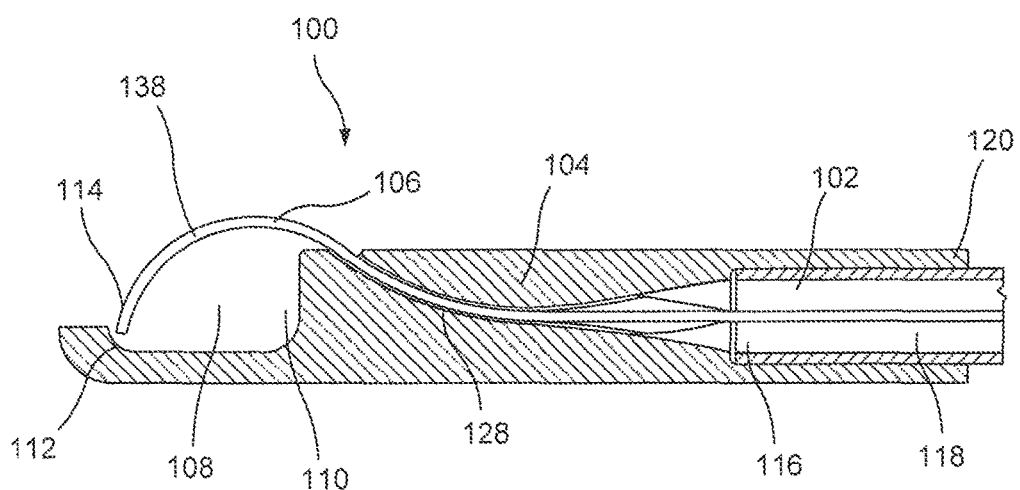
FIG. 5 shows a longitudinal cross-sectional view of a device according to another exemplary embodiment of the present disclosure.

The distal member 104 is connected to the distal end 116 of the elongate body 102. In one example, as shown in FIGS. 1 and 2, a proximal end 120 of the distal member 104 includes a connecting portion 126 sized and shaped to be received within the channel 118. The distal member 104, however, may be connected to the elongate body 102 in any of a number of ways. In another example, as shown in FIG. 5, the distal member 104 is mounted over the distal end 116 of the elongate body 102. In another embodiment, the distal member 104 may be integrally formed with the elongate body 102.

The distal member 104 extends longitudinally from the proximal end 120 to a distal end 122 and forms an elongated recess 108 extending along a portion of a length of a sidewall 134 thereof from the proximal end 110 to the distal end 112. The distal member 104 includes a lumen 128 extending therethrough, in communication with the channel 118. The lumen 128 is sized and shaped to slidably receive the cutting element 106 therethrough. In one embodiment, as will be described in further detail below, the lumen 128 is curved along a length thereof to accommodate a correspondingly curved cutting element 106. In particular, the lumen 128 according to this embodiment is curved from a proximal opening 130 at the proximal end 120 of distal member 104 to a distal opening 132 through a portion of the sidewall 134 of the distal member 104 proximal of the proximal end 110 of the recess 108 and open thereto. The distal opening 132 is configured as a trough through the sidewall 134 which prevents the cutting element 106 from rotating out of plane as the cutting element 106 is moved from the open configuration to the closed configuration.

The distal end 112 of the distal member 104 includes a receiving feature 124 sized and shaped to receive the distal end 114 of the cutting element 106, when the cutting element 106 is moved to the closed configuration. The receiving feature 124 limits a distal extension of the cutting element 106 to prevent excessive distal extension of the cutting element 106 which may result in the cutting of non-targeted tissue. The receiving feature 124 may be, for example, a pocket or groove sized, shaped and oriented to receive the distal end 114 of the cutting element 106. In some embodiments, the receiving feature 124 may include a nonconductive and/or thermally insulative member to protect adjacent non-targeted tissue. In another embodiment, where an energy source provided to the cutting element 106 is a bipolar current, the receiving feature 124 may include a return path for conducting electrical energy as would be understood by those skilled in the art. The receiving feature 124 may also be configured to prevent the cutting element 106 from becoming dislodged therefrom when the tissue received within the recess 108 applies a force thereto and/or as the device 100 is moved to cut the target tissue received within the recess 108. For example, the receiving feature 124 may be shaped with an overhang to prevent the cutting element 106 from being dislodged therefrom once it is received in the receiving feature 124. In one embodiment, the receiving feature 124 may include a conical shape and/or angled or curved surfaces for guiding the distal end 114 of the cutting element 106 thereinto. In addition, as described above, the distal opening 132 through the sidewall 134 prevents the cutting element 106 from being rotated out of plane as the cutting element 106 is moved toward the closed configuration. Thus, the distal end 114 of the cutting element 116 is guided into the receiving feature 124 as the cutting element 106 is moved toward the closed configuration.

As discussed above, the cutting element 106 may be energized by any of a variety of energy sources (e.g., radio frequency, monopolar or bipolar AC or DC current, laser, ultrasonic or infrasonic energy) connected, for example, to the proximal end of the cutting element 106. In one exemplary embodiment, the cutting element 106 may be a wire receiving electrical current therethrough for cutting the target tissue via cauterization. The cutting element is movable between the open configuration, in which the distal end 114 thereof is proximate the proximal end 110 of the recess 108, and the closed configuration, in which the distal end 114 is moved distally relative to the distal member 104 toward the receiving feature 124. In one embodiment, the distal end 114 may be entirely retractable into the lumen 128 of the distal member 114 to further prevent inadvertent cutting during insertion and positioning of the device. Thus, tissue received within the recess 108 and gripped between the distal end 114 of the cutting element 106 and the receiving element 124, when the cutting element 106 is in the closed configuration, is severed from surrounding tissue and the wound at the point of separation of the tissue sample is cauterized via the energy provided to the distal end 114.

The cutting element 106 according to this embodiment extends along a curved shaped so that, when the device 100 is in the closed configuration, a distal portion 138 of the cutting element 106 extends distally from the distal opening 132 around the recess 108 (extending radially outward from the exterior surface 136 of the distal member 104 to enlarge the tissue receiving area formed by the recess 108 and then curves back toward the distal member 104 to enter the receiving feature 124. In other words, the distal portion 138 of the cutting element 106, which extends distally past the distal opening 132 of the lumen 128, has a generally hook-like shape. The cutting element 106 may be, for example, heat-set, formed or bent to have the curved configuration using any known method. The cutting element 106 may be formed of a shape memory material. The curvature of the cutting element 106 allows the cutting element 106 to move between the open and closed configurations along an arcuate path to allow more room for tissue to be received within the recess 108.

Since the distal portion 138 of the cutting element 106 is curved, the cutting element 106 includes features for maintaining a desired alignment of the cutting element 106 relative to the distal member 104. In other words, the cutting element 106 maintains an orientation and planar direction of movement relative to the lumen 128 of the distal member 104 to ensure that the distal end of the cutting element 108 enters the receiving feature when fully extended distally. In one embodiment, at least a portion of the cutting element 106 may be keyed to a portion of the lumen 128. For example, as shown in FIG. 5, the cutting element 106 may have a rectangular cross-section, which is slidably received within a correspondingly sized and shaped portion of the lumen 128. Alternatively, the cutting element 106 may include a single planar surface slidably along a correspondingly planar surface of the lumen 128. In another embodiment, the cutting element 106 may include an overtube extending over a portion thereof. The overtube may key to a portion of the lumen 128 so that the overtube slidably engages the lumen 128 as the overtube is advanced and/or retracted relative to the distal member 104 to move the cutting element 106 between the open and closed configurations. This keying feature also prevents the cutting element 106 from being rotated out of plane so that the distal end 114 of the cutting element 106 is guided into the receiving feature 124 as the cutting element 106 is moved toward the closed configuration.

Although the exemplary embodiments show and describe the cutting element 106 as energy based, in another embodiment (not shown) the cutting element 106 may be mechanical. For example, the cutting element 106 may include a blade, saw, or other cutting edge which cuts tissue received within the recess 108 and gripped between the distal end 112 thereof and the distal end 114 of the cutting element 106.

According to an exemplary method using the device 100, the device 100 may be inserted into a living body to a target tissue via, for example, a working channel of an endoscope, until the distal member 104 is proximate the target tissue. The device 100 may be inserted to the target tissue with the cutting element 106 in the open configuration. The distal member 104 is positioned proximate the target tissue so that the target tissue is received within the recess 108. Upon receipt of the target tissue in the recess 108, the cutting element 106 is moved distally relative to the distal member 104, toward the closed configuration, so that the target tissue is gripped between the distal end 112 of the recess 108 and the distal end 114 of the cutting element. As described above, an energy source such as, for example, an electrical current is applied through the cutting element 106 so that the distal end 114 cuts the target tissue in contact therewith via cauterization. The cutting element 106 cuts the tissue as the cutting element 106 is moved toward the closed configuration. In another embodiment, once the target tissue has been received win the recess 108 and the cutting element 106 has been moved to the closed configuration, the entire device 100 can be moved proximally to cut through the tissue that was captured in the recess 108. The device 100 may also be moved laterally to cut additional tissue to the side of the initial cut. This allows the device to be used as a knife cutting longer paths. In another example, the device 100 may be rotated about a longitudinal axis thereof to excise an annular portion of tissue. Once the distal end 114 is received within the receiving element 124 at the distal end 112 of the recess 108, however, the cutting element 106 is prevented from cutting any tissue therebeyond. Once the target tissue has been cut, as desired, the cutting element 106 may be moved to the open configuration so that the above-described process may be repeated for a second portion of target tissue, if desired. Upon cutting of all the desired tissue, the device 100 may be removed from the body as would be understood by those skilled in the art. Once the device 100 has been removed, a separate device may be inserted to the target site to retrieve the cut tissue. Alternatively, prior to removal of the device 100, the cutting element 106 may be used to grip or harpoon the cut tissue to drag the cut tissue out of the body as the device 100 is being withdrawn from the body. In this embodiment, the energy source is deactivated so as not to further cut the tissue as it is being removed from the body.

It will be apparent to those skilled in the art that various modifications may be made in the present disclosure, without departing from the scope of the disclosure. Thus, it is intended that the present disclosure cover modifications and variations of this disclosure provided that they come within the scope of the appended claims and their equivalents.

What is claimed is:

1. A tissue cutting device, comprising:
    a flexible elongate body extending longitudinally from a proximal end to a distal end and including a channel extending longitudinally therethrough;
    a distal member connected to the distal end of the elongate body, the distal member including a lumen extending therethrough in communication with the channel and a recess extending through an exterior surface of the distal member along a portion of a length thereof, the recess extending from a recess proximal end to a recess distal end which includes a receiving structure; and
    a cutting element slidably received within the channel and the lumen so that the cutting element is movable between an open tissue-receiving configuration, in which a distal end of the cutting element in its entirety is proximal of the recess, and a closed tissue-gripping configuration, in which a distal portion of the cutting element extends across the recess such that the distal end of the cutting element is moved toward the recess distal end to be received within the receiving structure, a portion of a length of the distal portion of the cutting element extending radially beyond an exterior surface of the distal member.

2. The device of claim 1, wherein the cutting element is connected to an energy source at a proximal end of the cutting element so energy is provided along a length of the cutting element to cut tissue via the distal end of the cutting element.

3. The device of claim 2, wherein the energy source supplies one of radio frequency energy, a direct current, an alternating current, laser light, ultrasonic energy and infrasonic energy.

4. The device of claim 1, wherein the receiving structure is one of a pocket and a groove.

5. The device of claim 1, wherein the receiving structure is shaped to prevent the cutting element from being dislodged therefrom when tissue received within the recess applies a force to the cutting element.

6. The device of claim 1, wherein the distal portion of the cutting element, in the closed tissue-gripping configuration, has a curved configuration in which the distal portion of the cutting element extends distally out of the lumen and curves outward beyond the exterior surface of the distal member, the distal end of the cutting element curving back toward the receiving structure of the recess.

7. The device of claim 6, wherein the exterior surface of the distal member includes a trough to support the cutting element in the curved configuration and to maintain an orientation and a planar directional movement of the cutting element relative to the distal member.

8. The device of claim 1, wherein the distal portion of the cutting element is substantially hook-shaped.

9. The device of claim 1, wherein the receiving structure is electrically insulated.

10. The device of claim 3, wherein the receiving structure forms a return path for electrical energy.

11. The device of claim 1, wherein the cutting element is keyed to the lumen to maintain an orientation and a planar directional movement of the cutting element relative to the distal member.

12. A device for cauterizing tissue, comprising:
    an elongate body extending longitudinally from a proximal end to a distal end and including a channel extending longitudinally therethrough;
    a distal member connected to the distal end of the elongate body, the distal member including a lumen extending therethrough in communication with the channel and a recess extending through an exterior surface of the distal member along a portion of a length thereof, the recess extending from a recess proximal end to a recess distal end which includes a receiving structure;
    a cutting wire slidably received within the channel and the lumen so that the cutting wire is movable between an open tissue-receiving configuration, in which a distal end of the cutting wire in its entirety is proximal of the recess, and a closed tissue-gripping configuration, in which a distal portion of the cutting wire extends across the recess such that the distal end of the cutting wire is moved toward the distal end of the recess to be received within the receiving structure; and
    an energy source connected to the proximal end of the cutting wire to provide an electrical current therethrough so that the distal end of the cutting wire cuts a target tissue gripped between the distal end of the cutting wire and the distal end of the recess in the closed tissue-gripping configuration.

13. The device of claim 12, wherein the distal portion of the cutting element, in the closed tissue-gripping configuration, has a curved configuration in which the distal portion of the cutting wire extends distally out of the lumen and curves outward beyond an exterior surface of the distal member, the distal end of the cutting element curving back toward the receiving structure of the recess.

14. The device of claim 12, wherein the cutting wire is keyed to the lumen of the distal member to maintain an orientation and a planar directional movement of the cutting wire relative to the distal member.

15. The device of claim 12, wherein the receiving structure is electrically insulated.

16. A method for cutting tissue, comprising:
    inserting a cutting device into a living body to a target tissue via a working channel of an endoscope, the cutting device including a distal member having a lumen extending through a portion thereof and a recess extending through an exterior surface along a portion of a length thereof;
    receiving the target tissue in the recess of the distal member;
    sliding a cutting element within the distal member from an open configuration, in which a distal end of the cutting element in its entirety is proximal of the recess, to a closed configuration, in which a distal portion of the cutting element extends across the recess such that the distal end of the cutting element is moved toward the distal end of the recess to be received within a receiving structure at the distal end of the recess to grip the target tissue therebetween; and applying energy along a length of the cutting element to cut the target tissue received within the recess.

17. The method of claim 16, further comprising moving the device laterally or proximally relative to the endoscope to cut tissue.

18. The method of claim 16, further comprising rotating the device about a longitudinal axis thereof to excise an annular portion of tissue.

19. The method of claim 16, wherein a distal portion of the cutting element, in the closed configuration, has a curved configuration in which the distal portion of the cutting element extends distally out of the lumen and curves outward beyond an exterior surface of the distal member, the distal end of the cutting element curving back toward the receiving structure of the recess.

20. The method of claim 16, wherein the cutting wire is keyed to the lumen of the distal member to maintain an orientation and a planar directional movement of the cutting wire relative to the distal member.

\* \* \* \* \*